United States Patent [19]

Schick et al.

[11] 4,107,060
[45] Aug. 15, 1978

[54] LUBRICANT COMPOSITIONS CONTAINING BIOCIDAL, ANTIRUST ADDITIVES

[75] Inventors: John W. Schick, Cherry Hill; Robert H. Davis, Pitman, both of N.J.

[73] Assignee: Mobil Oil Corporation, New York, N.Y.

[21] Appl. No.: 783,239

[22] Filed: Mar. 31, 1977

Related U.S. Application Data

[63] Continuation-in-part of Ser. No. 587,761, Jun. 17, 1975, abandoned, which is a continuation-in-part of Ser. No. 353,178, Apr. 20, 1973, abandoned.

[51] Int. Cl.² .............................................. C10M 1/06
[52] U.S. Cl. .................................. 252/49.3; 252/49.5; 252/49.7; 252/51.5 R; 260/308 B; 424/269
[58] Field of Search ............... 252/49.7, 50, 51.5 R, 252/49.3, 49.5; 260/300 B; 424/269

[56] References Cited

U.S. PATENT DOCUMENTS

| | | | |
|---|---|---|---|
| 2,501,649 | 3/1950 | Wright | 260/308 B |
| 3,265,620 | 8/1966 | Heiman | 252/49.3 X |
| 3,374,171 | 3/1968 | Davis | 252/49.3 X |
| 3,527,704 | 9/1970 | Perilstein et al. | 252/49.7 |
| 3,564,001 | 2/1971 | Long | 260/308 B |
| 3,849,433 | 11/1974 | Butala | 260/308 B |
| 3,897,351 | 7/1975 | Davis et al. | 253/49.3 X |
| 3,986,967 | 10/1976 | Okorodudu | 260/308 B X |
| 4,014,894 | 3/1977 | Andress | 260/308 B |

*Primary Examiner*—Delbert E. Gantz
*Assistant Examiner*—Andrew H. Metz
*Attorney, Agent, or Firm*—Charles A. Huggett; Raymond W. Barclay; Thomas S. Szatkowski

[57] ABSTRACT

Compounds having biocidal and antirust properties which constitute the reaction product of (a) a benzotriazole compound having the formula:

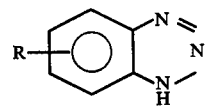

wherein R is hydrogen or an alkyl group containing from about 1 to about 6 carbon atoms and (b) a water soluble base, characterized by a basicity greater than that of said benzotriazole compound, such as an alkali metal hydroxide or a hydrocarbyl amine. Lubricant compositions are also provided containing biocidal and antirust amounts of the aforenoted reaction product.

13 Claims, No Drawings

LUBRICANT COMPOSITIONS CONTAINING BIOCIDAL, ANTIRUST ADDITIVES

CROSS-REFERENCE TO RELATED APPLICATIONS

This application is a continuation-in-part of application Ser. No. 587,761, filed June 17, 1975, now abandoned, which is a continuation-in-part of application Ser. No. 353,178, filed Apr. 20, 1973, now abandoned.

BACKGROUND OF THE INVENTION

1. Field of the Invention

This invention relates to lubricant additives and to improved lubricant compositions and, in one of its aspects, relates more particularly to lubricant compositions which exhibit improved biocidal and anti-rust properties and also non-ferrous metal deactivation properties. Still more particularly, in this aspect, the invention relates to lubricant compositions in the form of oleagineous, aqueous and emulsion metal working fluids which are normally subject to one or more of the aforementioned characteristics of biocidal and rust formation, and also metal deterioration properties.

2. Description of the Prior Art

It is well-known that certain types of lubricants, including, for example, metal working fluids, are susceptible to microbial degradation, rust formation and other forms of metal deterioration in the course of performing their intended functions.

Various additive materials have been suggested by the prior art to overcome these shortcomings. Thus, U.S. Pat. No. 3,597,353, of Randell et.al., disclosed the use of 4,5,6,7-tetrahydrobenzotriazole as a metal deactivating additive for natural and synthetic lubricants. Similarly, U.S. Pat. No. 3,413,227 of Howard et.al. teaches that an alkyl-substituted benzotriazole containing an alkyl group of from 2 to 20 carbon atoms or an alkyanoylamine group containing from 3 to 20 carbon atoms can be used as corrosion or tarnish inhibitors.

Alkanolamines such as 2-amino-2-ethyl-1,3-propanediol, tertiary amines such as tri-n-butylamine, and alkali metal nitrites such as sodium nitrite are disclosed as rust inhibitors for soluble oil compositions in U.S. Pat. No. 3,201,349 of Quanstrom. U.S. Pat. No. 2,655,478 of Deutser et al. teaches that soluble oils can be inhibited against corrosion of steel by adding small amounts of an aliphatic alkylene polyamine having from 3 to 20 carbon atoms.

The above patents disclose the separate use of benzotriazoles or amines in lubricants as corrosion inhibitors. There is no teaching or suggestion of the present invention that a benzotriazole and a water soluble base react to form a product which exhibits improved biocidal properties. Indeed, the prior art cited above teaches that the incorporation of known bactericides is necessary to provide compositions with desired biocidal properties.

In U.S. Pat. No. 3,788,993 of Andress, it is taught that benzotriazoles react with alkyl or alkenyl succinic anhydrides to form reaction products which impart corrosion inhibiting the properties to lubricating oils. Such disclosure of the reaction of benzotriazole with an acid (or anhydride) highlights the difference between the prior art reactions and those of the present invention, where benzotriazole is reacted with a basic material. The significance of such differences will be discussed in greater detail hereinafter. British Pat. No. 995,708 discloses an aqueous metal working fluid which comprises an aqueous solution containing a polyoxyalkylene glycol, as well as salt of an alkanolamine and a dibasic carboxylic acid. It also discloses that small amounts of benzotriazole can also be included in the fluid as a metal deactivator. The lack of biocidal properties exhibited by the fluids of this patent is evident from specific disclosure directed to the desirability of adding bactercides. U.S. Pat. No. 3,374,171 of Davis also teaches the failure of compositions similar to those of the British Patent in exhibiting biocidal properties.

Finally, U.S. Pat. No. 3,265,620 of Heiman, describes a concentrate of triethanolamine, sodium nitrite, and a small amount of benzotriazole to which an amino polycarboxylic acid chelating agent is preferably added. As those skilled in the art are aware, the presence of sodium nitrite would contribute to, rather than inhibit, the growth of bacteria.

Thus, the prior art discloses products which are different than the reaction products of the present invention and which do not exhibit the biocidal properties of the novel reaction product described and claimed herein.

SUMMARY OF THE INVENTION

It has now been found that an additive which consists essentially of the reaction product of a benzotriazole compound having the formula:

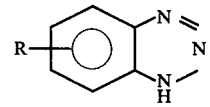

where R is hydrogen or an alkyl group containing from about 1 to about 6 carbon atoms and a water soluble base, characterized by a basicity greater than that of said benzotriazole compound, such as an alkali metal hydroxide or a hydrocarbyl amine, when incorporated into lubricant compositions, imparts improved biocidal and rust preventive properties to the composition.

The reaction product of the present invention is generally employed in biocidal and rust preventive amounts. As one skilled in the art is aware, the actual amount employed will vary depending upon the particular application and the characteristic of the lubricant into which the reaction product is incorporated. For most applications, however, the reaction product is employed in amounts from about 0.001 to about 75%, by weight, of the total lubricant composition.

Where the lubricant comprises an aqueous fluid, the reaction product is preferably employed in amounts from about 1% to about 70% by weight of the total composition, with amounts from about 5% to about 70%, by weight, being particularly preferred. Such aqueous fluids are primarily utilized as coolants in metalworking operations.

Where the lubricant comprises an oleaginous material such as an oil of lubricating viscosity, the lubricant may comprise any mineral or synthetic oil of lubricating viscosity. In instances where high temperatures stability is not a prime requirement, mineral oil of a viscosity of at least 40 SSU. at 100° F. and particularly those falling within the range from about 60 SSU. to about 6,000 SSU. at 100° F. is preferably employed. In instances where the lubricant comprises a synthetic oil rather than a mineral oil, or in combination therewith, various compounds of this type may be successfully utilized.

Typical synthetic vehicles include: polypropylene glycol, trimethylol propane esters, neopentyl and pentaerythritol esters, di-(2-ethyl hexyl) sebacate, di-2(ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl) ether and phenoxy phenyl ethers.

The reaction product of the present invention is generally added to compositions which comprise the oleaginous materials described above in amounts from .01 to about 5%, by weight, and preferably from about 1 to about 4%, by weight.

Where the lubricant comprises emulsion metalworking fluids, the reaction product of the present invention may be employed in amounts from about 0.01 to about 20%, by weight, preferably from about 1 to about 10%. Emulsion metalworking fluids are known in the art by many names, including soluble oils, water miscible fluids, or emulsifiable cutting fluids. These fluids generally comprise a suspension of oil droplets in water and are made by blending an oil, which may generally be of the same type as the oleaginous materials described above, with water and emulsifying agents. The most common emulsion contains paraffin or naphthenic mineral oil which generally ranges in viscosity from 100 to 500 SUS at 100° F. Common emulsifiers include petroleum sulfonates, amine soaps and rosin soaps.

As hereinbefore described, a benzotriazole compound having the formula:

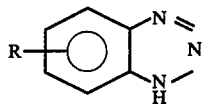

where R is hydrogen or an alkyl group containing from about 1 to about 6 carbon atoms may be reacted with a water soluble base, characterized by a basicity greater than that of said benzotriazole compound, such as an alkali metal hydroxide or a hydrocarbyl amine to form the desired reaction product additive.

Preferred benzotriazole compounds are benzotriazole and tolutriazole.

Representative of the hydrocarbyl amines are the aliphatic and alkanol amines. Aliphatic amines which may be employed to form the reaction products of the present invention include the mono-, di- and tri-alkyl amines where the alkyl group contains from about 1 to about 6 carbon atoms. Alkanol amines which may be employed include the mono, di, and tri-alkanol amines where the alkanol group contains from about 1 to about 8 carbon atoms. Preferred alkanol amines include the mono, di and tri-ethanol and isopropanol amines. Triethanol amine is particularly preferred. Alkali metal hydroxides such as sodium hydroxide, as well as other water-soluble base materials which are capable of reacting with benzotriazole or alkyl substituted benzotriazole may be employed.

In general, an excess of the water soluble base is reacted with the benzotriazole or alkyl substituted benzotriazole. Particularly comtemplated are mole ratios (base/benzotriazole compound) of from about 1/1 to about 5/1 with from 1/1 to about 2/1 being preferred. The reaction takes place at a temperature of from about 10° to about 90° C with a temperature of from 20° to about 70° C being preferred.

DESCRIPTION OF SPECIFIC EMBODIMENT

The following comparative data and examples will serve to illustrate the preparation of the aforementioned reaction product of a benzotriazole or an alkyl substituted benzotriazole with a water-soluble base, of the present invention, and to demonstrate the effectiveness of these reaction products in lubricant compositions which are normally susceptible to bacterial, anit-rust and metal deterioration properties and, their effect on metal surfaces with which they may normally come into contact, or which tend to undergo deterioration under conditions of use. It will be understood, of course, that it is not intended that the invention be limited to the particular compositions disclosed or to the operations or manipulations involved. Various modifications thereof can be employed and will be readily apparent to those skilled in the art.

In the comparative data of the following tables, the malleable iron rust test employed, in conjunction with 1-30 ASTM hard water, is described in detail in U.S. Pat. No. 3,374,171.

The biocidal activity test is conducted as follows:

In this procedure ½ inch × ½ inch × 0.027 inch thick filter paper is saturated with the biocidal test solution (approximately ¼ ml.). This square is placed in the center of a nutrient agar plate previously inoculated with bacteria (predominantly pseudomonas). In this test an effective biocidal agent should inhibit growth adjacent to the filter paper. The distance from the edge of the paper to the point where bacterial growth begins, is indicative of activity. The data recorded in the tables with respect to reactant and water components is in per cent, by weight.

Table I

| Example | 1 | 2 |
|---|---|---|
| Triethanolamine | 68 | 45 |
| Benzotriazole |  | 23 |
| Water | 32 | 32 |
| Biocide Activity Test Bacterial Growth Inhibition |  |  |
| Inches From Test Square | 1/16 | 5/16 |
| Malleable Iron Rust Test |  |  |
| 1-30 ASTM Hard Water | Rust | No Rust |

As will be seen from the comparative data of the foregoing table, the reaction product of triethanolamine and benzotriazole was markedly superior to the use of triethanolamine alone in inhibiting bacterial growth and in rust prevention.

Table II

| Example | 3 | 4 |
|---|---|---|
| Triethanolamine | 45 |  |
| Sodium Hydroxide |  | 7.73 |
| Benzotriazole |  | 23.00 |
| Tolutriazole | 23 |  |
| Water | 32 | 69.27 |
| Biocide Activity Test Bacterial Growth Inhibition |  |  |
| Inches from square | ½ | ½ |
| Malleable Iron Rust Test |  |  |
| 1-30 ASTM Hard Water | Trace | Trace |

From the foregoing table, the efficacy of the reaction products of benzotriazole or tolutriazole with a water-soluble base, in inhibiting bacterial growth and in rust prevention, will be apparent.

While not wishing to be bound by any theory, an examination of the chemistry of these materials will point out the reactions which it is believed occur in forming the novel reaction products of the present invention. First, it is important to realize that benzotriazoles are amphoteric i.e. they can react as both an acid and a base. This will become apparent to one skilled in the chemical art by an examination of the structure of benzotriazole:

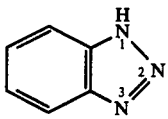

Since the hydrogen atom which is attached to the first nitrogen may be given to a strong base, the material can act as an acid. Also, since the second and third nitrogens can accept hydrogen atoms from other compounds, the material can act as a base.

The prior art, namely U.S. Pat. No. 3,788,993 of Andress shows benzotriazole acting as a base by accepting a hydrogen from an organic acid to form a salt. The following reaction mechanism is illustrative of the prior art teachings:

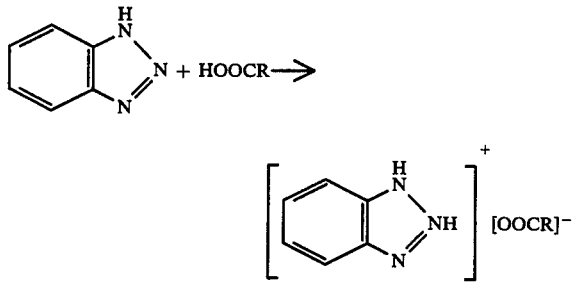

However, in the presence of a base of sufficient strength, benzotriazole can react by giving up its hydrogen to the stronger base. A reaction such as this is believed to occur in the formation of the reaction products of the present invention. It may be illustrated as follows:

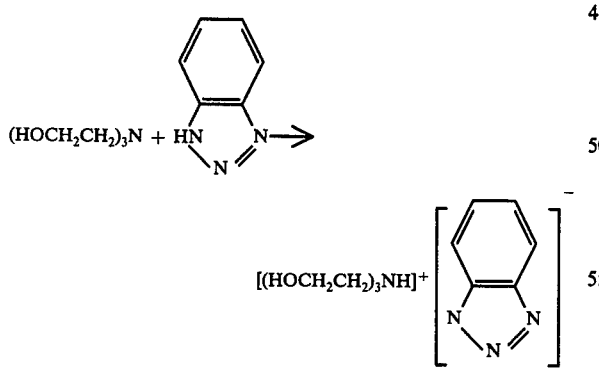

For this reaction to occur, the strength (or relative basicity) of the base which draws the hydrogen in from the benzotriazole (i.e. triethanolamine in the above equation) must be greater than the corresponding basic strength of the benzotriazole. Triethanolamine, for example, has a relative basicity of approximately at least ten times greater than that of benzotriazole.

Finally, if there be any doubt that the reaction just described does in fact occur, it is noted that benzotriazole is normally only slightly soluble in water. Yet, as shown in Table I, Example 2, 23% by weight of this material was incorporated into water. Such would not be possible if the benzotriazole did not form a reaction product with the triethanolamine.

Further, it has been found that in the ultraviolet spectrum a reaction product is produced, for example, between benzotriazole and triethanolamine. More specifically, it is noted that the absorption spectrum of a solution that contains two compounds that do not react with each other will be the same as that obtained by adding together the absorption spectrum of each of the individual compounds. However, if the two compounds react, the shape of the absorption spectrum of the solution will be different. Some peaks will become smaller or larger or will shift to a different wavelength. If these changes occur in the visible part of the spectrum the eye sees an overall change in the color of the solution. For instance, a pH indicator changes from blue to yellow when changing from a basic to an acid form. When such a change occurs in the ultraviolet region, the effects must be measured instrumentally.

With the above in mind, the ultraviolet absorption spectrum of benzotriazole in water was measured. This showed a peak at 262 nm and a shoulder at 276 nm. The spectrum of triethanolamine in water showed no peaks. The absorbance was almost nil above 280 nm; below 280 nm there was a gradual increase in general absorption. The summation of the two absorption curves if no reaction occurs would show a slight increase in the height of the 262 nm peak relative to the 276 nm shoulder. This did not occur.

The absorption spectrum of the solution containing both benzotriazole and triethanolamine in water showed, instead, a decrease in the height of the 262 nm peak relative to the 276 nm shoulder. A small peak appears at 273 nm. In essence, therefore, although these effects are small, they do show that benzotriazole and triethanolamine react to form a species that is different from the starting materials. The composition under investigation comprised 45%, by weight, triethanolamine; 23%, by weight, benzotriazole; and 32%, by weight, water.

From the foregoing discussion, it is evident that the presence of a acidic material in the benzotriazole - water soluble base material system would prevent the formation of the reaction products of the present invention. Thus, in British Pat. No. 995,708 where compositions containing an alkanolamine, carboxylic acid and small amounts of benzotriazole are disclosed, the presence of the acid would promote the following reactions:

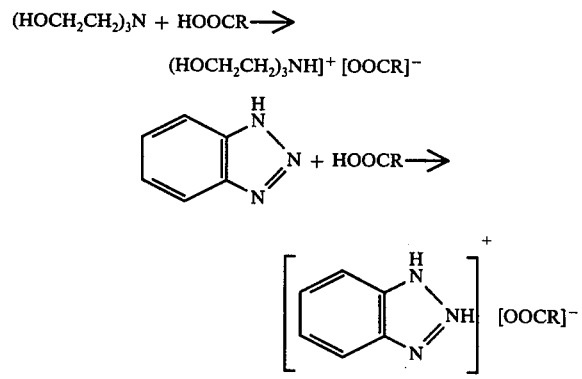

and prevent the formation of the reaction products of the present invention. It is postulated that the inability of the prior art compositions to exhibit biocidal properties is due to the prevention of the formation of the novel reaction products of the present invention.

It will be understood that although the present invention has been described with preferred embodiments, various modifications and adaptations thereof may be resorted to without departing from the spirt of the invention as those skilled in the art will readily understand.

We claim:

1. A composition which comprises a lubricant base selected from the group consisting of oils of lubricating viscosity, water, and emulsions thereof; and in a biocidal and rust preventative amount, an additive consisting essentially of the reaction product of (a) a benzotriazole compound having the formula:

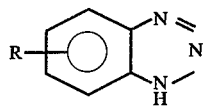

where R is hydrogen or an alkyl group containing from about 1 to about 6 carbon atoms and (b) a water soluble base, characterized by a basicity greater than that of said benzotriazole compound, which is selected from the group consisting of alkanol and hydrocarbylamines wherein said water soluble base is reacted with said benzotriazole in mole proportions from about 1:1 to about 5:1 and at a temperature of from about 10° to about 90° C.

2. The composition of claim 1 wherein said hydrocarbyl amine comprises an aliphatic amine.

3. The composition of claim 1 wherein said lubricant base comprises water.

4. The composition of claim 1 wherein said reaction product is present in an amount from about 0.001 to about 75% by weight.

5. The composition of claim 1 wherein said reaction product is that obtained by the reaction of benzotriazole and triethanolamine.

6. The composition of claim 1 wherein said reaction product is that obtained by the reaction of tolutriazole and triethanol amine.

7. The composition of claim 1 wherein said alkanol amine contains from about 1 to about 8 carbon atoms.

8. The reaction product of (a) a benzotriazole compound having the formula:

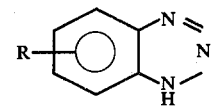

where R is hydrogen or an alkyl group containing from about 1 to about 6 carbon atoms and (b) a water soluble base, characterized by a basicity greater than that of said benzotriazole compound, which is selected from the group consisting of alkanol and hydrocarbyl amines wherein said water soluble base is reacted with said benzotriazole in mole proportions of from 1:1 to about 5:1 and at a temperature of from about 10° to about 90° C.

9. The reaction product of claim 8 wherein said hydrocarbyl amine comprises a aliphatic amine.

10. The reaction product of claim 8 wherein said alkanol amine comprises triethanolamine.

11. The reaction product of claim 8 wherein the benzotriazole compound is tolutriazole.

12. The reaction product of claim 8 wherein said alkanol amine contains from about 1 to about 8 carbon atoms.

13. The reaction product of claim 8 wherein said benzotriazole compound is benzotriazole and said water soluble base is triethanol amine.

* * * * *